(12) United States Patent
Steck (10) Patent No.: US 6,521,267 B1
(45) Date of Patent: Feb. 18, 2003

(54) TYROSINASE INHIBITORS FROM PLANTS

(75) Inventor: Warren Steck, Saskatchewan (CA)

(73) Assignee: Fytokem Prtoducts, Inc., Saskatchewan (CA)

( * ) Notice: Subject to any disclaimer, the term of this patent is extended or adjusted under 35 U.S.C. 154(b) by 0 days.

(21) Appl. No.: 09/719,205

(22) PCT Filed: Jun. 8, 1999

(86) PCT No.: PCT/CA99/00530

§ 371 (c)(1), (2), (4) Date: Apr. 9, 2001

(87) PCT Pub. No.: WO99/64025

PCT Pub. Date: Dec. 16, 1999

Related U.S. Application Data (60) Provisional application No. 60/088,484, filed on Jun. 8, 1998.

(51) Int. Cl.[7] .......................... A61K 35/78; A61K 7/135
(52) U.S. Cl. .......................................... 424/725; 424/62
(58) Field of Search ................................ 424/764, 725, 424/62

(56) References Cited

U.S. PATENT DOCUMENTS

| | | | |
|---|---|---|---|
| 5,980,904 A | * | 11/1999 | Leverett et al. |
| 6,068,834 A | * | 5/2000 | Kvalnes et al. |
| 6,174,533 B1 | * | 1/2001 | SaNoguira et al. |

FOREIGN PATENT DOCUMENTS

| | | |
|---|---|---|
| JP | 57-163307 | 10/1982 |
| JP | 60-214721 | 10/1985 |
| JP | 62-029528 | 2/1987 |
| JP | 01-3110011 | 12/1989 |
| JP | 03-127714 | 5/1991 |
| JP | 04-300812 | 10/1992 |
| JP | 08-012565 | 1/1996 |
| JP | 08-067615 | 3/1996 |
| JP | 08-099859 | 4/1996 |
| JP | 08-104646 | 4/1996 |

OTHER PUBLICATIONS

Oenothera biennis L. (http://res2.agr.ca/london/pmrc/english/herbs/oenothera.html.*
Kim et al. Biological Screening of 100 Plant Extracts for Cosmetic Use (1): Inhibitory Activities of Tyrosinase and DOPA Auto–Oxidation International Journal of Cosmetic Science 19, 291–298 (1997).
Iida et al. Potent Inhibitors of Tyrosinase Activity and Melanin Biosysnthesis From Rheum Officinale Planta Med. 61 425–428 (1995).
Jimenez et al. 4–Substituted Resorcinols (Sulfite Alternatives) As Slow–Binding Inhibitors of Tyrosinase Catecholase Activity Journal of Agricultural Food Chemistry 45, 2061–2065 (1997).
Mason, H.S. J. Biol. Chem. 172, 83–86 (1948).
Balin, A.K., and Kligman, A.M. Aging and the Skin Raven Prss, NY pp. 372 (1989).
Dawson, C.S. and Magee, R.J. Methods in Enzymology II S.P. Colowick and N.O. Caplan, eds. 817–827 (1955).
Lerner, A.B. Methods in Enzymology II S.P. Colowick and N.O. Caplan, eds. 827–831 (1955).
Bergemeyer, U.H. Methods of Enzymtic Analysis Verlag Chemie, Weinheim (1983).

* cited by examiner

*Primary Examiner*—Christopher R. Tate
*Assistant Examiner*—Randall Winston
(74) *Attorney, Agent, or Firm*—Frommer, Lawrence & Haug; Thomas J. Kowalski (57) ABSTRACT

The present invention provides tyrosinase inhibiting extracts from dictotyledonous plant species indigenous to Canada and compositions containing the extracts for the treatment of skin, particularly skin lightening. The present invention also provides a method of detecting tyrosinase activity in an extract of a dicotyledonous plant species indigenous to Canada.

38 Claims, 6 Drawing Sheets

FIG. 5

TYROSINASE INHIBITORS FROM PLANTS

RELATED APPLICATIONS

This application is the national phase of PCT/CA99/00530, filed Jun. 8, 1999, designating the U.S. and published as WO 99/64025, claiming priority from U.S. patent application Ser. No. 60/088,484, filed Jun. 8, 1998. All of the foregoing applications, as well as all documents cited in the foregoing applications ("application documents") and all documents cited or referenced in application documents are hereby incorporated herein by reference. Also, all documents cited in this application ("herein cited documents") and all documents cited or referenced in herein cited documents are hereby incorporated herein by reference.

FIELD OF THE INVENTION

The invention relates to a product comprising a tyrosinase inhibiting extract derived from a dicotyledonous plant species indigenous to Canada. The present invention also relates to compositions comprising the product and a suitable diluent or carrier for the treatment of skin or of fruit, vegetables or beverages. The present invention further relates to a method for identifying plant extracts that are capable of inhibiting the enzyme tyrosinase.

BACKGROUND OF THE INVENTION

Tyrosinase (tyrosine oxidase, EC 1.10.3.1) is an enzyme or closely homologous group of enzymes of universal occurrence in microbes, plants and animals. Its primary metabolic function is to catalyze the oxidative degradation of the amino acid tyrosine. This degradation takes slightly different routes in animals, plants and microbes, but the rate-controlling first steps—those catalyzed by tyrosinase—are the same in virtually all living species. In animals, including man, tyrosinase first transforms tyrosine into 3,4-dihydroxyphenylalanine (DOPA), thence to the corresponding quinone (DOPAquinone), and finally to 2-carboxy-2,3-dihydroindole-5,6-quinone (DOPAchrome) which is further converted by other enzymes to still more highly oxidized materials which include the melanin substances responsible for skin pigmentation.

Skin pigmentation thus depends upon the action of tyrosinase. If this enzyme is not active, normal pigmentation does not occur, and skin loses or fails to acquire its normal tan-to-brown coloration. The effect is independent of racial or environmental factors. Pigmentation loss manifests itself in lentigo senile, so-called "age spots", a small-scale, patchy color loss often seen in skin of people over 50 years of age; typically the de-pigmented patches will be 1–3 mm across and can be very numerous. A more serious effect is leucodenna, a group of diseases in which large areas of skin lose their melanin and appear pink. An extreme effect is albinism, a condition in which tyrosinase enzyme is entirely dysfunctional and no pigmentation of skin (or eyes or hair) occurs.

If on the other hand tyrosinase activity is accelerated, as in sun-tanning or in some pathological conditions, the amount of melanin formed increases and skin color darkens. When the distribution of the new melanin is even and controlled, the result is a "glorious bronzed body"; but if the new melanin is patchy or produced uncontrollably, the result is pathological. Skin melanomas are sites of localized hyperactivity by tyrosinase; they are often associated with cancerous cell modification. The causal relationship of tyrosinase action to skin pigmentation was established many years ago (Mason, H. S. (1948) J. Biol. Chem. 172, 83–86; Balin, A. K. and Kligman, A. M. (1989) Aging and the Skin 372pp, Raven Press, N.Y.) and is now well-understood.

Materials which suppress the action of tyrosine oxidase are presumed to slow the build-up of skin spots over time, and this presumption is vindicated by scientific evidence. Thus, the correlation between tyrosinase inhibition and protection of skin against unwanted pigmentation is accepted by the medical profession and by the cosmetic industry.

In addition to its skin functions, tyrosinase is active in other types of living tissue in the turnover metabolism of tyrosine and in the production of pigmented materials in those tissues.

With respect to cosmetics, skin lightening and skin darkening have been practiced since earliest times, and today these are mainstays of some sectors of the world cosmetics industry. Skin lightening has traditionally been accomplished by rigorously excluding sunlight from skin, or by the use of chemical lightening agents. One such agent is synthetic hydroquinone (1,4-dihydroxybenzene). This substance is considered the cosmetic industry standard for tyrosinase inhibition potency.

SUMMARY OF THE INVENTION

Prior to the present invention, the possibility of finding effective tyrosinase inhibitors in dicotyledonous plant species indigenous to Canada had not been appreciated.

Accordingly, the present invention provides a product comprising an extract derived from a dicotyledonous plant species indigenous to Canada, wherein the extract inhibits tyrosinase. Preferably, the extract is derived from a plant species selected from Polygonaceae, Rosaceae and Onagraceae. The extract is preferably derived from one or more parts of the plant selected from leaves, twigs, flowers, flowering aerials, fruiting aerials, seeding aerials, roots and fruits.

Preferably, the extract is derived from the group consisting of:

flowering aerials of *Artemisia campestris* (plains wormwood);

flowering aerials of *Aster ericoides* (white prairie aster);

flowering aerials of *Aster hesperius* (willow aster);

leaves, twigs and flowers of *Cornus stolonifera* (red-osier dogwood);

leaves and twigs of *Cotoneaster acutifolia* (cotoneaster);

flowering aerials of *Epilobium angustifolium* (fireweed);

seeding aerials of *Euphorbia esula* (leafy spurge);

fruiting aerials of *Fragaria americana* (wild strawberry);

fruiting aerials of *Fragaria glauca* (Wild strawberry);

flowering aerials of *Geranium bicknelli* (Bicknell's geranium);

flowering aerials of *Geum aleppicum* (yellow avens);

flowering aerials of *Geum triflorum* (3-flowered avens);

flowering aerials of *Glycyrrhiza lepidota* (wild licorice);

flowering aerials of *Hedysarum americanum* (American hedysarum);

roots of *Heuchera richardsonii* (alumroot);

flowering aerials of *Oenothera biennis* (yellow evening-primrose); flowering aerials of *Polygonum persicaria* (lady's-thumb);

flowering aerials of *Potentilla fruticosa* (shrubby cinquefoil);

flowering aerials of *Potentilla norvegica* (rough cinquefoil);

flowering aerials of *Rosa acicularis* (prairie rose);

fruiting aerials of *Rosa arkansana* (low rose);

fruiting aerials of *Rumex maritimus* (golden dock);

fruiting aerials and flowering aerials of *Rumex occidentalis* (western field dock);

fruiting aerials and fruits of *Rumex pseudonatronatus* (field dock); and fruits of *Rumex stenophyllus* (narrow-leaved dock).

The present invention also provides a composition comprising the product as defined herein, together with a cosmetically or pharmaceutically acceptable, or edible, diluent or carrier. The composition is preferably for cosmetic treatment of skin or for inhibiting browning of edible products. The composition is more preferably for skin lightening, even more preferably to reduce melanin and/or melanogenesis. The at least one plant extract in the composition is preferably selected from the group consisting of:

fruiting aerials of *Rumex maritimus* (golden dock);

fruiting aerials of *Rumex occidentalis* (western field dock);

flowering aerials of *Rumex occidentalis* (western field dock);

fruiting aerials of *Rumex pseudonatronatus* (field dock);

fruits of *Rumex pseudonatronatus* (field dock); and fruits of *Rumex stenophyllus* (narrow-leaved dock).

The present invention also provides a method for detecting tyrosinase inhibiting activity in an extract derived from a dicotyledonous plant species indigenous to Canada. This method comprises:

a) preparing a first solution comprising an amount of tyrosinase and a suitable substrate;

b) preparing a second solution comprising the same amount of tyrosinase and the suitable substrate and further comprising an amount of the extract;

c) measuring tyrosinase activities of the first and second solutions by suitable methods;

d) comparing the tyrosinase activities of the first and second solutions; and e) detecting tyrosinase inhibiting activity, present when the tyrosinase activity of the second solution is less than the tyrosinase activity of the first solution.

It is preferable that the tyrosinase inhibiting activity is comparable to, or greater than, that of hydroquinone.

DESCRIPTION OF THE PREFERRED EMBODIMENTS

The definitions of various terms used in this specification appear below.

"Plant extracts" are substances obtained from plants by physical separation processes such as solvent extraction, steam distillation, or pressing. Broadly, the term "extract" may sometimes be extended to include the solvent as well as the plant substance dissolved in it.

The term "screening test" refers to any simple and standardized test whose purpose is to separate or screen out, from a large number of materials, those unable to perform the function upon which the test is based, from those able to perform that function.

A typical pilot scale plant extraction method for Rumex species is provided below.

Ripe, dry (post-season) Rumex species, mostly R. Occidentalis, were field collected and dry-milled into small fragments. These (250 kg) were extracted at 70° C. for one hour with 2000 L of approximately 70% ethanol in water. An orange extract was separated from the mash by decantation and the latter was washed with a further 1000 L of 70% alcohol. The extract liquids were combined, filtered and concentrated to 50 L, by which point the ethanol had virtually all been removed and extract solids (content 18–20%) were then beginning to precipitate out. Alternatively, 50 L of glycerol or 1,3-butanediol was added to the partly concentrated solution to provide a final concentration end-point volume of 100 L. This approach avoids precipitation of extract solids.

Carrier glycerol (or 1,3-butanediol) and water were added to the concentrate to make a red-coloured solution having 5% solids content. Then a further amount of 1:1 glycerol (or 1,3-butanediol)-water carrier liquid was added, amounting to 25% of the weight of the 5% solution and itself containing 5% of L-ascorbic acid (Vitamin C) as an anti-colorant and anti-oxidant. Finally, an anti-microbial preservative, such as phenoxyethanol, was added to a concentration of 0.3 to 0.4%.

The above method provides the basis for the method used to produce the other extracts of the invention. A person skilled in the art will understand that variation in certain parameters and substances used in the method will still produce an extract of the invention.

The tyrosinase assay was based on methods previously published (Mason, H. S., (1948) J. Biol. Chem. 172, 83–86; Dawson, C. R. and Magee, R. J. (1955) Methods in Enzymology II 817–827 (Editors-in-chief S. P. Colowick and N. O. Caplan); Lerner, A. B. (1955) ibid 827–831; Bergmeyer, U. H. (1983) Methods of Enzymatic Analysis (Published by Verlag Chemie, Weinheim)). The protocol was as follows, scaled for the approximately twenty sample determinations:

(a) A buffer solution of pH 6.5 was prepared by dissolving 1.4 9 disodium monohydrogen phosphate ($Na_2HPO_4$) and 1.4 g monopotassium dihydrogen phosphate ($KH_2PO_4$) in pure water to make 200 mL.

(b) An enzyme solution of either 1.0 mg or 3.0 mg tyrosinase (Sigma T-7755) was prepared in 30 mL buffer and stored at 2° C. until use.

(c) A substrate solution was prepared by dissolving 0.10 g L-DOPA (L-3,4-dihydroxyphenyl-alanine, Sigma D-9661) in 100 ML buffer.

(d) The unfettered enzyme reaction rate was measured by mixing together 0.5 mL buffer solution and 0.5 mL substrate solution in twin acrylate mini-cuvettes (path 2.0 mm), and after observing the stability of the mixture, mixing in 0.25 mL enzyme solution to one cuvette. The formation of red DOPAquinone was monitored spectrophotometrically at 475 nm, at times 0, 1, 2 and 3 minutes.

(e) The effect of added substances on the enzyme reaction rate was measured by mixing together 0.5 mL buffer solution, 0.5 mL substrate solution and 0.25 mL test substance (at 1% strength in 50:50 butyleneglycol:water) in twin acrylate mini-cuvette. The reaction was tracked spectrophotometrically at 475 nm, reading at 0, 1, 2 and 3 minutes.

(f) The effect of test substances on reaction rate was expressed as inhibition (I) where I=100−[100 (trt absorbance change, 3 min)/100(control absorbance change, 3 min)].

Concentrations of substrate, enzyme or test substance can be varied as appropriate.

Figure 1:
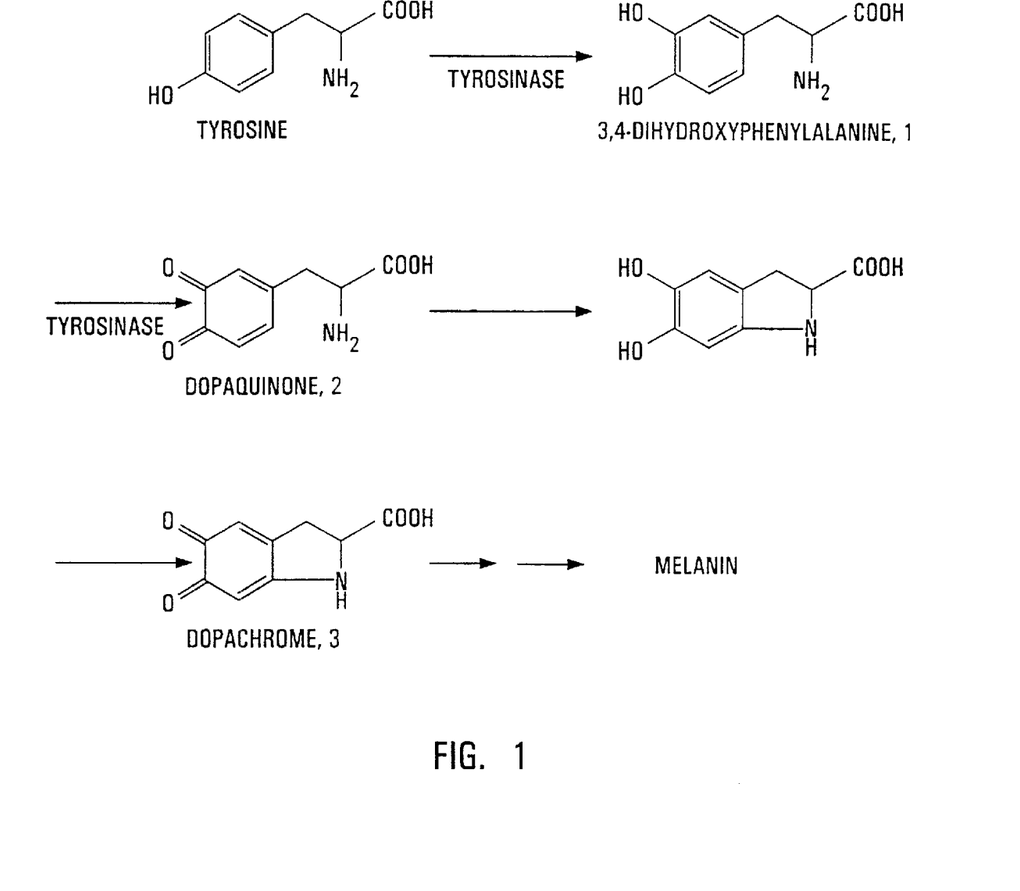
FIG. 1 is summary of the main steps in the biogenesis of melanin from tyrosine.
Figure 2A:
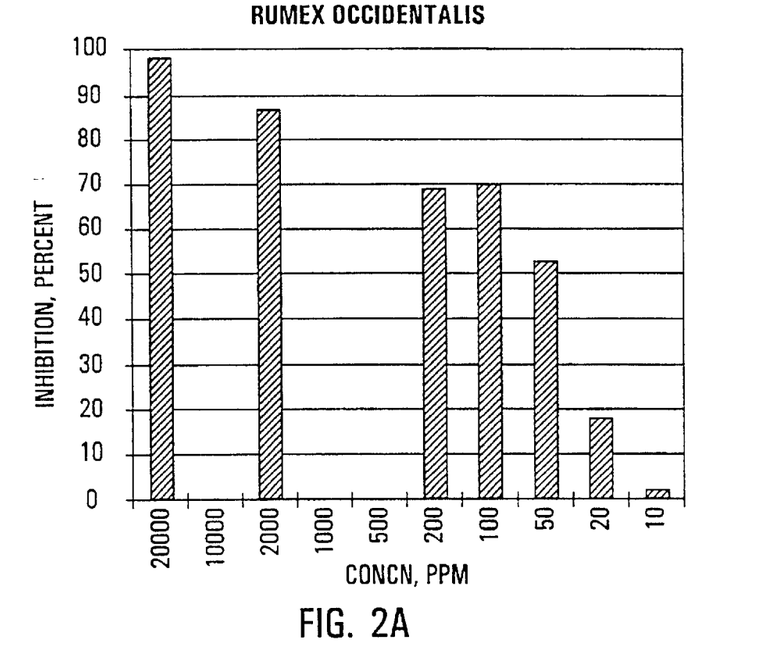
FIG. 2 is a plot of "percent inhibition of enzyme action" vs. log "percent extract in assay reaction mixture" indicating the effectiveness of extracts of Rumex pseudonatronatus, Rumex occidentalis and Oenothera biennis as tyrosinase inhibitors. Tyrosinase—5 mg. Standard-hydroquinone.
Figure 2B:
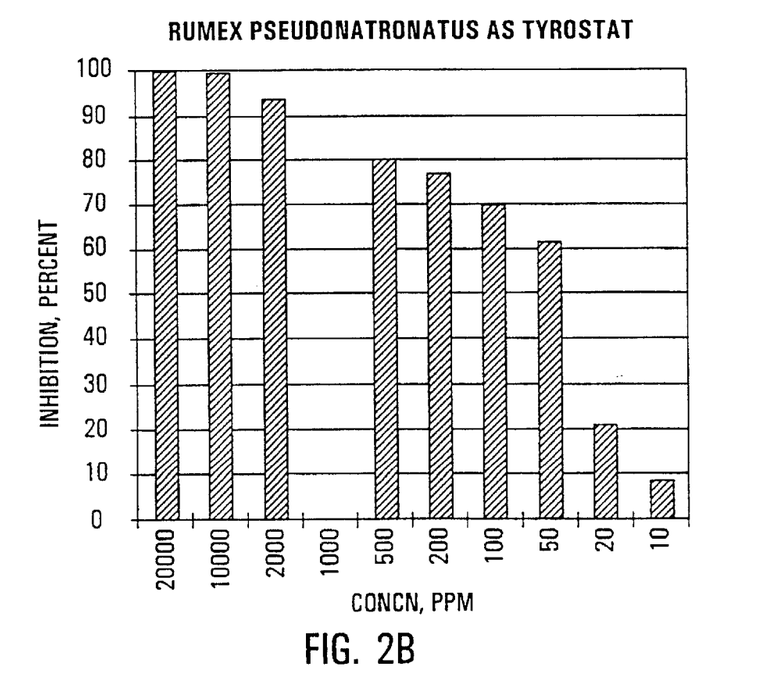
Figure 2C:
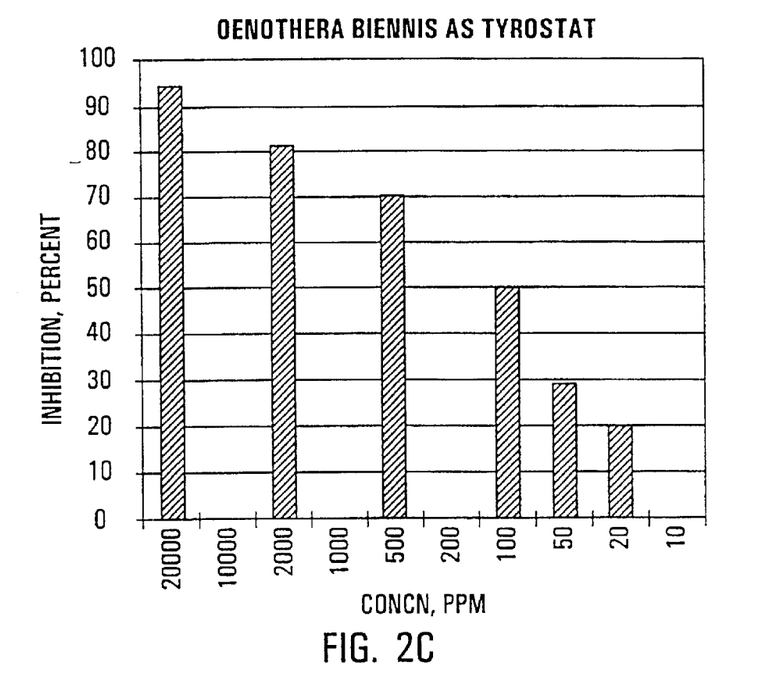
Figure 2D:
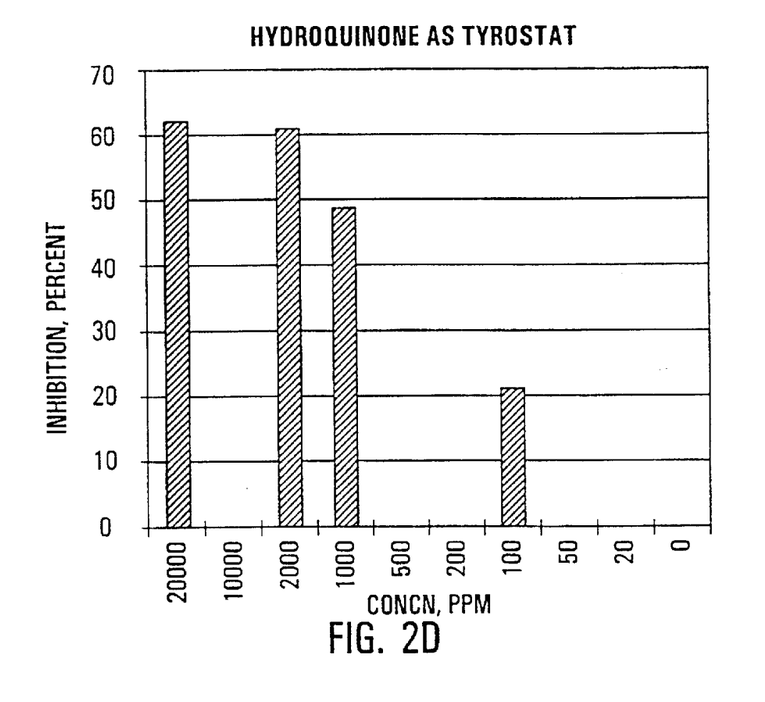
Figure 3A:
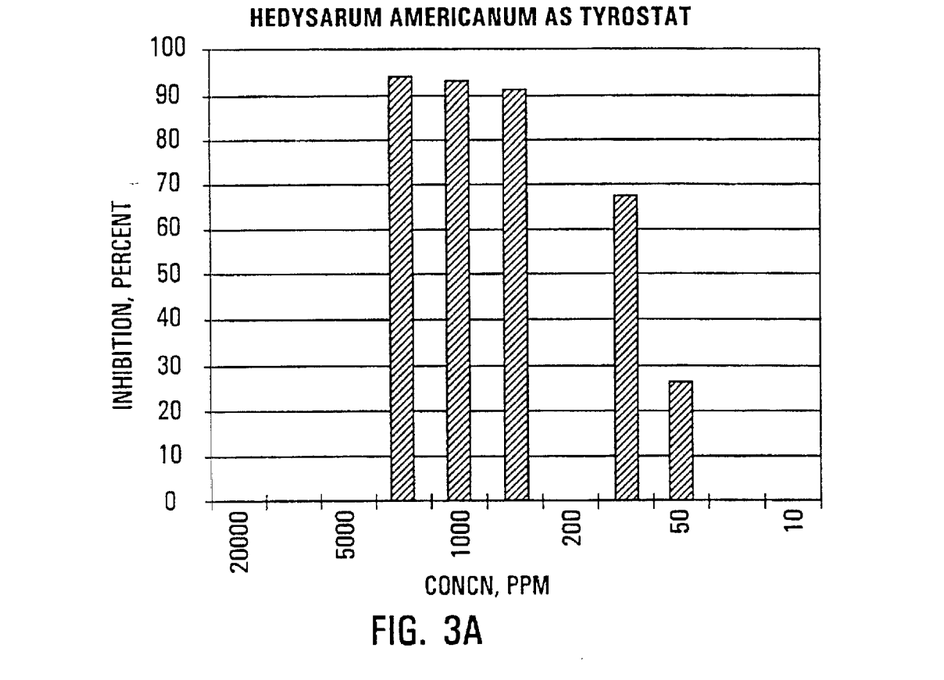
FIG. 3 is a plot of "percent inhibition of enzyme action" vs. log "percent extract in assay reaction mixture" indicating the effectiveness of extracts of Hedysarum americanum and Rosa acicularis as tyrosinase inhibitors. Tyrosinase—5 mg. Standard—hydroquinone.
Figure 3B:
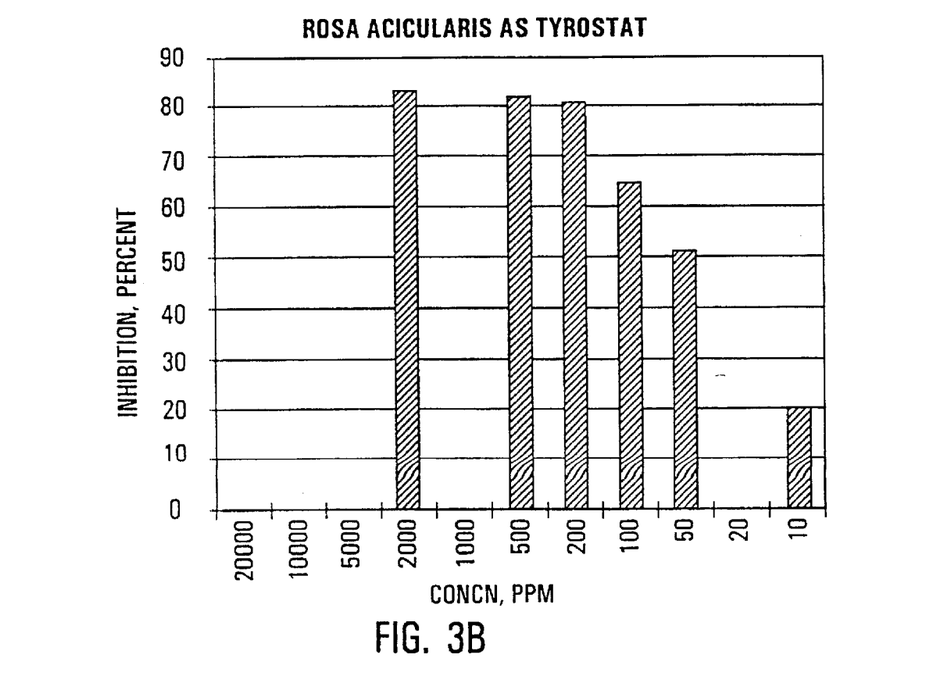
Figure 4:
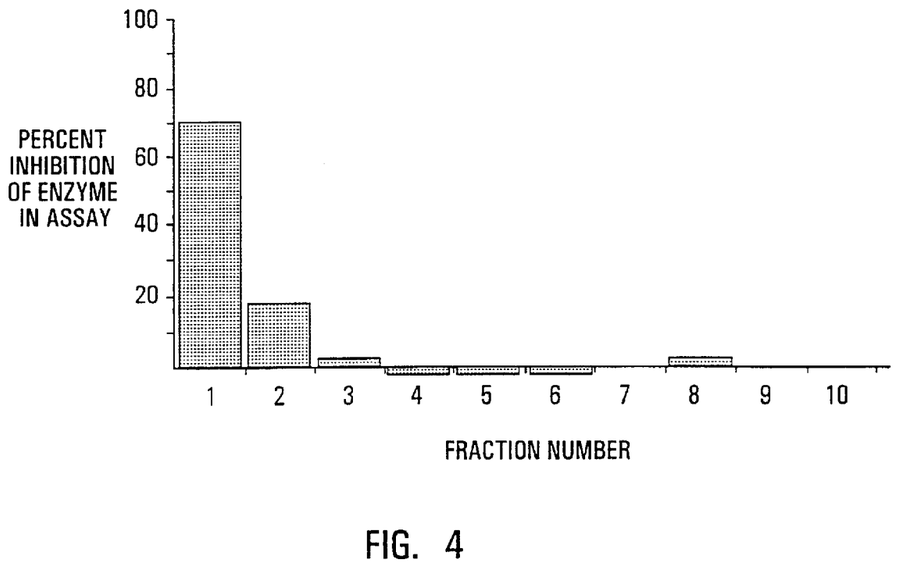
FIG. 4 shows the elution profile of whole extract of Rumex pseudonatronatus from a polyvinylpyrrolidone chromatographic column in terms of percent inhibition of tyrosinase in the assay. Elution was with water (ff 1–4) and water-ethanol gradient (ff 5–10).

Plant extracts screened by the method of the invention were selected which exhibited tyrosinase inhibiting potency equal to, or better than, hydroquinone. Those extracts are listed in Table 1. The concentration dependence of the potency of various extracts is summarized in FIGS. 2 and 3 in comparison to the concentration dependence of the potency of hydroquinone.

Figure 5:
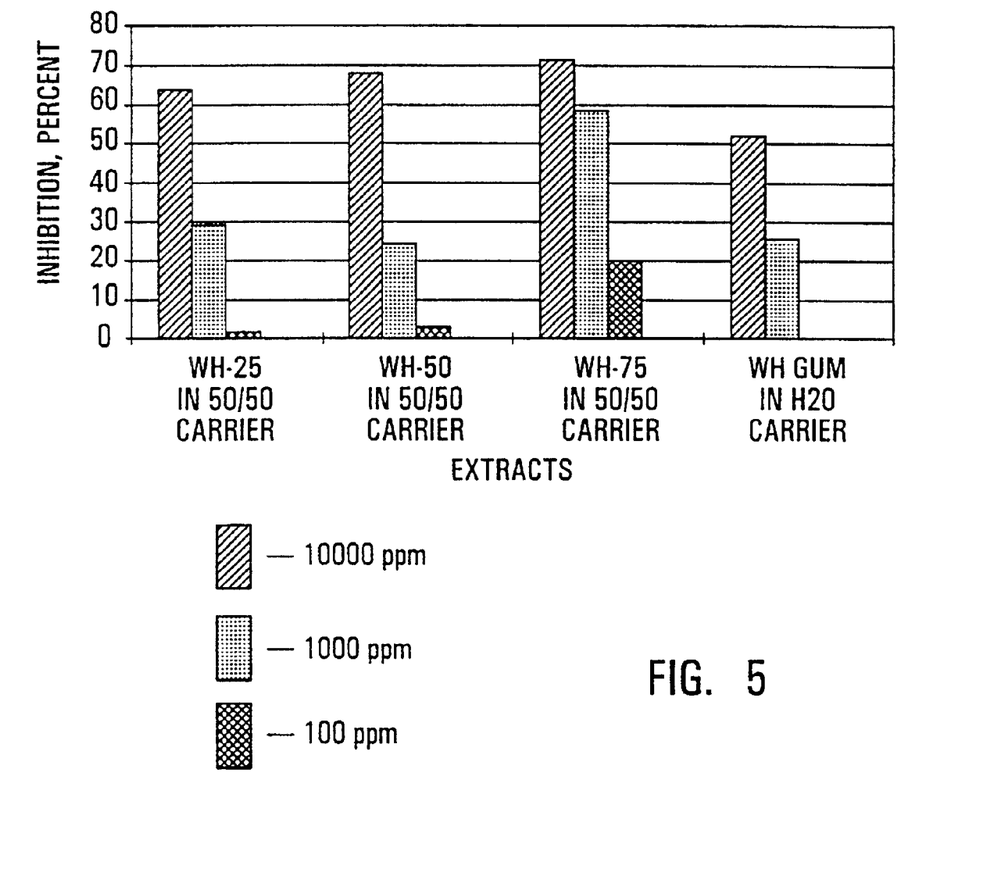
FIG. 5 shows the effect of alcohol in the extraction solvent on tyrosinase inhibiting activity from Epilobium angustifolium. Epilobium angustifolium (=WH) was extracted using water (WH-00), 25% ethanol (WH-25), 50% ethanol (WH-50), 75% ethanol (WH-75) and 95% ethanol (WH-95). Each extract was assayed for tyrosinase inhibitory power at three concentrations. The carrier was butanediol and water.

Table 2 shows the effect of varying the extraction solvent on the tyrosinase inhibiting activity of extracts from three different plant species. The effect is also shown by the results in FIG. 5.

TABLE 1

Plant extracts and phytochemicals with tyrosinastatic power equal to or greater than that of hydroquinone

| Plant botanical name<br>Standard: pure HYDROQUINONE @ 1% | Common name | Parts used | Enzymes reaction rate reduction @ 5 μg enzyme 65% | @ 15 μg enzyme 55% |
|---|---|---|---|---|
| PLANT EXTRACTS OF | | | | |
| *Amalanchier alnifolia* | Saskatoonberry | flwrg, leaves & twigs | 83%, 85% | nd |
| *Artemisia campestris* | plains wormwood | flowering aerials | nd | 65% |
| *Aster ericoides* | white prairie aster | flowering aerials | nd | 78% |
| *Aster hesperius* | willow aster | flowering aerials | 66% | nd |
| *Cornus stolonifera* | red-osier dogwood | leaves, twigs, flowers | 79% | 60% |
| *Cotoneaster acutifolia* | cotoneaster | leaves & twigs | 65% | nd |
| *Epilobium angustifolium A* | firewood | flowering aerials | 70% | 61% |
| *Epilobium angustifolium B* | firewood | flowering aerials | 82% | nd |
| *Euphorbia esula* | leafy spurge | seeding aerials | nd | 58% |
| *Fragaria americana* | wild strawberry | fruiting aerials | nd | 61% |
| *Fragaria glauca* | wild strawberry | fruiting aerials | 77%, 68% | 72% |
| *Geranium bicknelli* | Bicknell's geranium | flowering aerials | 64% | 61% |
| *Geum aleppicum* | yellow avens | flowering aerials | 78% | 67% |
| *Geum triflorum* | 3-flowered avens | flowering aerials | 78% | 71% |
| *Glycyrrhiza lepidota A* | wild licorice | flowering aerials | 76% | nd |
| *Hedysarum americanum B* | American hedysarum | flowering aerials | 93%, 87%, 90% | 88% |
| *Heuchera richardsonii* | alumroot | roots | 90% | 72% |
| *Oenothera biennis* | yellow evening-primrose | flowering aerials | 82% | 67% |
| *Polygonum persicaria* | lady's-thumb | flowering aerials | 90% | 73% |
| *Potentilla fruticosa* | shrubby cinquefoil | flowering aerials | 83%, 78% | |
| *Potentilla norvegica* | rough cinquefoil | flowering aerials | 78% | 74% |
| *Rosa acicularis* | prairie rose | flowering aerials | 83% | 83% |
| *Rosa arkansana* | low rose | fruiting aerials | 81% | 61% |
| *Rumex maritimus* | golden dock | fruiting aerials | 90% | 81% |
| *Rumex occidentalis A* | western field dock | fruiting aerials | 87% | 71% |
| *Rumex occidentalis B* | western field dock | flowering aerials | nd | 82% |
| *Rumex pseudonatronatus A* | field dock | fruiting aerials | 92% | 77% |
| *Rumex pseudonatronatus B* | field dock | fruits | 88% | 70% |
| *Rumex stenophyllus* | narrow-leaved dock | fruits | 88% | 69% |

TABLE 2

Extractability of tyrosinastatic activity from plants
The grid numbers are the percent inhibitions of the enzyme function obtained using each extracted solution in two standard tyrosinase assays
(5 μg enzyme). Data are corrected for ethanol effects.

| | EXTRACTION SOLVENT | | | |
|---|---|---|---|---|
| SPECIES | Ethanol | 1:1 Water-ethanol | Water | Ethyl acetate |
| Epilobium angustifolium (aerials) | 45%, 39% | 65%, 62% | 80%, 75% | <10% |

TABLE 2-continued

Extractability of tyrosinastatic activity from plants
The grid numbers are the percent inhibitions of the enzyme function
obtained using each extracted solution in two standard tyrosinase assays
(5 µg enzyme). Data are corrected for ethanol effects.

| SPECIES | EXTRACTION SOLVENT | | | |
|---|---|---|---|---|
| | Ethanol | 1:1 Water-ethanol | Water | Ethyl acetate |
| Oenothera biennis (aerials) | <10% | 58%, 67% | 66%, 63% | <101% |
| Rumex occidentalis (ripe aerials) | 54%, 48% | 79%, 79% | 81%, 84% | <10% |

There is a very large market for consumer goods containing natural products, such as plant extracts. Compositions for treatment of skin may be prepared comprising a tyrosinase inhibiting plant extract as disclosed herein, together with an acceptable diluent or carrier. Acceptable diluent or carriers for cosmetic applications can include such substances as water, aqueous alcohols, glycerol, propanediol and butanediol, as well as certain silicones and waxes. Acceptable diluents or carriers for pharmaceutical applications are well known in the art.

The tyrosinase inhibiting plant extract can also be used to treat fruit, vegetables or beverages to prevent or reduce browning, since tyrosinase activity is a contributor to the browning process. Compositions may be prepared to treat edible products such as fruit, vegetables or beverages to inhibit browning, which composition comprises a tyrosinase inhibiting plant extract as disclosed herein, together with a diluent or carrier that is suitable for consumption. The diluent or carrier suitable for consumption can include such substances as water, aqueous alcohols, propanediol and butanediol, as well as any other suitable substance acceptable by law.

EXAMPLE 1

A composition known as TYROSTAT-10 (T-10) has the following ingredients:

| | |
|---|---|
| Purified water | 45–50% |
| 1,3-butanediol | 45–50% |
| Plant extract solids (Canadian Rumex species) [Rumex occidentals, R. pseudonatronatus, R. stenophyllus and R. martimus] | 4.0–4.3% |
| L-Ascorbic acid | 0.9–1.1% |
| Phenoxyethanol (anti-fungal) | 0.2–0.3% |

The composition contains no added minerals or other organic materials. It is a readily pourable transparent solution, orange-red coloured at pH 4.0–7.5. Upon dilution, the colour moves toward pastel yellow. This colour darkens perceptibly but reversibly at pH values much above 8, and lightens perceptibly on long product storage when sealed from air.

The specific gravity is 1.05 at 21° C.

This material contains natural plant-sourced inhibitors of tyrosinase enzymes. The potency has been measured using in vitro assays of the conversion of DOPA (3,4-dihydroxyphenylalanine) to the corresponding quinone by the enzyme, in presence and in absence of the TYROSTAT product and the results are summarized in Table 3. This assay duplicates rate-controlling steps in the human metabolic pathway to skin pigmentation. Pure hydroquinone in 1% solution was employed as a comparison standard.

TABLE 3

| TESTED MATERIAL | SOLIDS PRESENT | INHIBITION OF ENZYME |
|---|---|---|
| Undiluted TYROSTAT-10 | 5% | 100% |
| TYROSTAT-10 diluted 10X | 0.5 | 100% |
| TYROSTAT-10 diluted 100X | 0.05 | 80–85% |
| Hydroquinone | 1.0 | 58–62% |

Rumex extracts appear to inhibit tyrosinase by binding or deforming the enzyme molecule around the active site. Ascorbic acid contributes to the overall inhibition by maintaining the enzyme's copper atoms in their reduced $Cu^+$ state. Other constituents of TYROSTAT-10 have no significant effect on tyrosinase in standard assays, although the carrier component butanediol is slightly inhibitory. The data in Table 4 indicate the relative capabilities of the active ingredients for tyrosinase inhibition, at various concentrations of the ingredients.

TABLE 4

| | Inhibition of tyrosinase enzyme step 2 | | | |
|---|---|---|---|---|
| Ingredient | 1% conc | 0.1% conc | 0.01% conc | 0.001% conc |
| Rumex extract | 81% | 69% | 53% | 38% |
| Ascorbic acid | 100% | 100% | 82% | 23% |
| [cf.hydroquinone] | 60% | 31% | <10% | <10% |

EXAMPLE 2

A composition known as TYROSTAT-11 (T-11) has the following ingredients:

| | |
|---|---|
| Purified Water | 45–50% |
| Glycerol | 45–50% |
| Plant extract solids (Canadian Rumex species) [Rumex occidentalis, R. pseudonatronatus, R. stenophyllus and R. martimus] | 4.0–4.3% |
| L-Ascorbic acid | 0.9–1.1% |
| Phenoxyethanol (anti-fungal) | 0.2–0.3% |

The composition contains no added minerals or other inorganic materials, and no synthetics other than phenoxyethanol preservative. It is a readily pourable transparent solution, orange-red coloured at pH 4.0–7.5. Upon dilution, the colour moves toward pastel yellow. This colour darkens perceptibly but reversibly at pH values much above 8, and lightens perceptibly on long product storage when sealed from air.

The specific gravity is 1.15 at 21° C.

This material contains natural plant-sourced inhibitors of tyrosinase enzymes. The potency has been measured using in vitro assays of the conversion of DOPA (3,4-dihydroxyphenylalanine) to the corresponding quinone by the enzyme, in the presence and in absence of the TYROSTAT product and the results are summarized in Table 5. This assay duplicates rate-controlling steps in the human metabolic pathway to skin pigmentation. Pure hydroquinone in 1% solution was employed as a comparison standard.

TABLE 5

| TESTED MATERIAL | SOLIDS PRESENT | INHIBITION OF ENZYME |
| --- | --- | --- |
| Undiluted TYROSTAT-11 | 5% | 100% |
| TYROSTAT-11 diluted 10X | 0.5 | 100% |
| TYROSTAT-11 diluted 100X | 0.05 | 80–83% |
| Hydroquinone | 1.0 | 38–62% |

Rumex extracts appear to inhibit tyrosinase by binding or deforming the enzyme molecule around the active site. Ascorbic acid contributes to the overall inhibition by maintaining the enzyme's copper atoms in their reduced $Cu^+$ state. Other constituents of TYROSTAT-11 have no significant effect on tyrosinase in standard assays. The data in Table 6 indicate the relative capabilities of the active ingredients for tyrosinase inhibition, at various concentrations of those ingredients.

TABLE 6

| | Inhibition of tyrosinase enzyme step 2 | | | |
| --- | --- | --- | --- | --- |
| Ingredient | 1% conc | 0.1% conc | 0.01% conc | 0.001% conc |
| Rumex extract | 81% | 69% | 53% | 38% |
| Ascorbic acid | 100% | 100% | 82% | 23% |
| [cf.hydroquinone] | 60% | 31% | <10% | <10% |

Numerous modifications and variations of the present invention are possible in light of the above teachings. It is therefore to be understood that within the scope of the appended claims, the invention may be practised otherwise than as specifically described herein.

What is claimed is:

1. A method of lightening skin, comprising administering to a human subject an effective amount of a Rumex plant extract obtained from a plant or plant part selected from the group consisting of *Rumex maritimus* (golden dock); *Rumex occidentalis* (western field dock); *Rumex pseudonatronatus* (field dock); and *Rumex stenophyllus* (narrow leaved dock), wherein the plant extract is a substance separated from the plant or plant part by a physical separation process, the physical separation process comprising:

(a) solvent extraction;
(b) steam distillation; or
(c) pressing.

2. The method of claim 1, wherein the physical separation process comprises solvent extraction.

3. The method of claim 2, wherein the solvent comprises an alcohol.

4. The method of claim 2, wherein the solvent comprises an alcohol and water.

5. The method of claim 1, wherein the physical separation process comprises steam distillation.

6. The method of claim 1, wherein the physical separation process comprises pressing.

7. The method of claim 2, wherein the plant extract is obtained from a plant part selected from the group consisting of fruiting aerials of *Rumex maritimus* (golden dock); fruiting aerials of *Rumex occidentalis* (western field dock); flowering aerials of *Rumex occidentalis* (western field dock); an aerial part of *Rumex occidentalis* (western field dock); fruiting aerials of *Rumex pseudonatronatus* (field dock); fruits of *Rumex pseudonatronatus* (field dock); and fruits of *Rumex stenophyllus* (narrow leaved dock).

8. The method of claim 7, wherein the plant part is the fruiting aerials of *Rumex maritimus* (golden dock).

9. The method of claim 7, wherein the plant part is the fruiting aerials of *Rumex occidentalis* (western field dock).

10. The method of claim 7, wherein the plant part is the flowering aerials of *Rumex occidentalis* (western field dock).

11. The method of claim 7, wherein the plant part is the fruiting aerials of *Rumex pseudonatronatus* (field dock).

12. The method of claim 7, wherein the plant part is the fruits of *Rumex pseudonatronatus* (field dock).

13. The method of claim 7, wherein the plant part is the fruits of *Rumex stenophyllus* (narrow leaved dock).

14. The method of claim 1, wherein the plant extract is combined with a cosmetically or pharmaceutically acceptable, or edible, diluent or carrier.

15. The method of claim 1, wherein the plant extract is applied to the skin of the subject.

16. The method of claim 1, wherein the plant extract is combined with ascorbic acid.

17. The method of claim 1, wherein the plant extract has a tyrosine inhibiting potency that is at least equal to that of hydroquinone.

18. The method of claim 2, wherein the plant extract has a tyrosine inhibiting potency that is at least equal to that of hydroquinone.

19. A method of lightening skin in a subject in need thereof due to accelerated tyrosinase activity, comprising administering an effective amount of Rumex plant extract obtained from a plant or plant part selected from the group consisting of *Rumex maritimus* (golden dock); *Rumex occidentalis* (western field dock); *Rumex pseudonatronatus* (field dock); and *Rumex stenophyllus* (narrow leaved dock), wherein the plant extract is obtained from the plant or plant part by a physical separation process, the physical separation process comprising:

(a) solvent extraction;
(b) steam distillation; or
(c) pressing.

20. The method of claim 19, wherein the physical separation process comprises solvent extraction.

21. The method of claim 20, wherein the solvent comprises an alcohol.

22. The method of claim 20, wherein the solvent comprises an alcohol and water.

23. The method of claim 19, wherein the physical separation process comprises steam distillation.

24. The method of claim 19, wherein the physical separation process comprises pressing.

25. The method of claim 18, wherein the subject is human.

26. The method of claim 19, wherein the plant is *Rumex occidentalis*.

27. The method of claim 19, wherein the plant extract is combined with a cosmetically or pharmaceutically acceptable$_4$o edible, diluent or carrier.

28. The method of claim 19, wherein the plant extract is applied to the skin of the subject.

29. A method of lightening skin by inhibiting tyrosinase activity in a subject in need thereof, comprising administering an effective amount of Rumex plant extract obtained from a plant or plant part selected from the group consisting of *Rumex maritimus* (golden dock); *Rumex occidentalis* (western field dock); *Rumex pseudonatronatus* (field dock); and *Rumex stenophyllus* (narrow leaved dock), wherein the plant extract is obtained from the plant or plant part by a physical separation process, the physical separation process comprising:

(a) solvent extraction;

(b) steam distillation; or (c) pressing.

30. The method of claim 29, wherein the physical separation process comprises solvent extraction.

31. The method of claim 30, wherein the solvent comprises an alcohol.

32. The method of claim 30, wherein the solvent comprises an alcohol and water.

33. The method of claim 29, wherein the physical separation process comprises steam distillation.

34. The method of claim 29, wherein the physical separation process comprises pressing.

35. The method of claim 29, wherein the subject is human.

36. The method of claim 29, wherein the plant is *Rumex occidentalis*.

37. The method of claim 29, wherein the plant extract is combined with a cosmetically or pharmaceutically acceptable, edible, diluent or carrier.

38. The method of claim 29, wherein the plant extract is applied to the skin of the subject.

* * * * *